United States Patent [19]

Shafiee et al.

[11] 4,114,314

[45] Sep. 19, 1978

[54] PROCESS FOR THE PRODUCTION OF THEBAINE

[75] Inventors: Ali Shafiee; Iraj Lalezari; Narges Yassa, all of Tehran, Iran

[73] Assignee: The Ministry of Science & Higher Education, Tehran, Iran

[21] Appl. No.: 770,307

[22] Filed: Feb. 22, 1977

[51] Int. Cl.² ............................................. A01G 1/00
[52] U.S. Cl. ........................................... 47/85; 260/285
[58] Field of Search ............................. 47/58; 260/285

[56] References Cited

PUBLICATIONS

Formation of Thebain — Kamimura et al., Plant Growth Reg. Abstracts, 1977, vol. 3, #6, p. 65.

Primary Examiner—Robert E. Bagwill
Attorney, Agent, or Firm—Omri. M. Behr

[57] ABSTRACT

Tissue cultures of cells from seed heads of Papaver bracteatum Lindl, Population Arya II, are grown in artificial nutrient media to produce thebaine which is then extracted therefrom. An example of an artificial nutrient medium used for the tissue culture is revised tobacco medium supplemented with 1% agar and 1ppm 2,4-dichlorophenoxyacetic acid.

7 Claims, No Drawings

PROCESS FOR THE PRODUCTION OF THEBAINE

FIELD OF THE INVENTION

This invention relates to a process for the production and isolation of thebaine, and to thebaine there produced.

DESCRIPTION OF THE PRIOR ART

Thebaine, whose composition $C_{19}H_{21}O_3N$ was established in 1852, is a member of the morphine group of alkaloids. Other members of the group include the medicinally useful drugs codeine ($C_{18}H_{21}O_3N$) and morphine itself ($C_{17}H_{19}O_3N$). Both codeine and morphine can be prepared from thebaine, for example, according to the following reaction scheme:

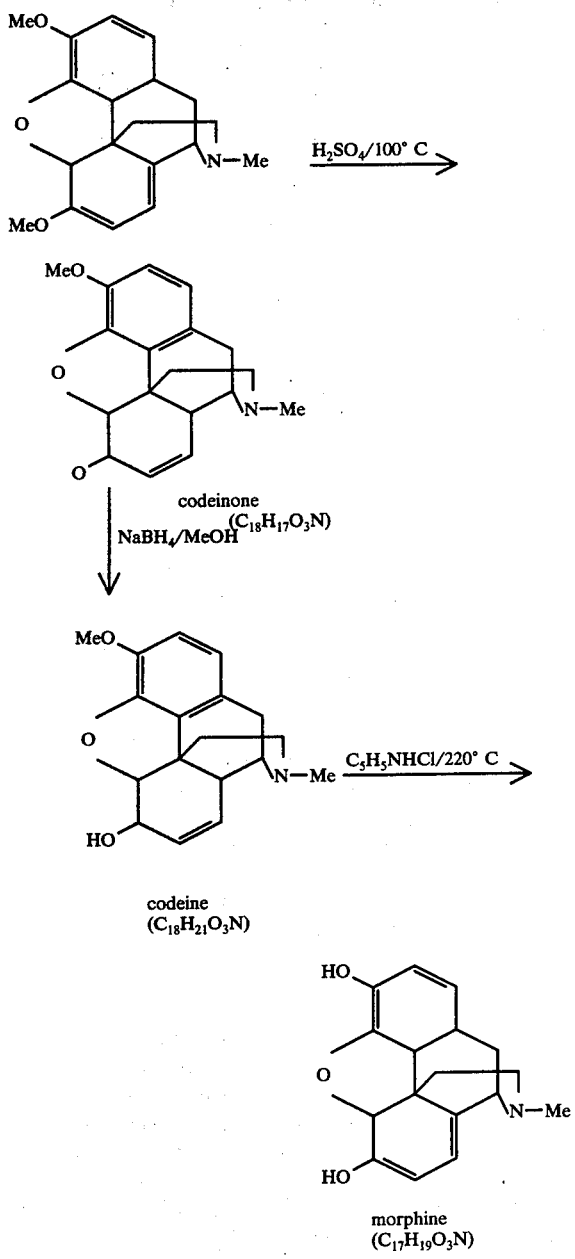

codeinone ($C_{18}H_{17}O_3N$)

codeine ($C_{18}H_{21}O_3N$)

morphine ($C_{17}H_{19}O_3N$)

The acid hydrolysis of thebaine to codeinone was first described by Knorr and Horlein (Ber. 1409 39 (1906)). They dissolved 3g thebaine in 30ccm 1N $H_2SO_4$ and, after boiling the solution for six to seven minutes, were able to extract ca. 0.15-0.2g codeinone (yield ∼ 7%). The low yield of codeinone is due to the ease with which thebaine undergoes rearrangement in acidic solution.

Gates (J.A.C.S. 4340 75 (1953)) has reported the nearly quantitative conversion of codeine to codeinone. He treated 0.194g codeinone in 10ccm MeOH and with 0.5g $NaBH_4$ suspended in 12ccm MeOH. After being allowed to stand for 1½ hours the resulting solution was concentrated to about half its original volume, then diluted with 10ccm 10% NaOH and momentarily boiled. After diluting the solution with water, 0.196g codiene were extracted with chloroform.

Rapoport et al. (J.A.C.S. 5485 and 5900 73 1951) have claimed a 22% yield of morphine from codeine employing pyridine hydrochloride as the cleavage agent. 1.00g codeine was heated with pyridine hydrochloride for six minutes under nitrogen. The reaction mixture was dissolved in 20ccm water, basified with 10ccm 4N NaOH and extracted with chloroform to yield 0.210g morphine.

Thebaine occurs naturally in a number of plants from which it can be extracted and purified by a somewhat expensive and laborious procedure. Thebaine-producing plants usually require special agronomical and environmental growing conditions which can further increase the final cost of the thebaine extracted therefrom. It has recently been reported, by one of the present inventors with two other authors (Lalezari, I., P. Nasseri, and R. Asgharian. 1974, Papaver bracteatum Lindl, Population Arya II, J. Pharm, Sci. 63:1331), that a population of Papaver bracteatum Lindl, named Arya II and found in Western Iran, produces thebain in amounts considerably greater than those present in previously known thebaine-containing plants. The name Arya II was adopted by the Second International Working Group on Papaver bracteatum: Sept 1973, Tehran, Iran (United Nations Secretariat Publication ST/SOA/SER, J/2 12 Sept 1973).

The technique of plant tissue culture is one in which plant cells are cultivated in a synthetic medium. Such artificially grown plant cells can have the potential of producing in vitro compounds which would be synthesised by the plant in growth. Examples of the technique and its application to the production of specific compounds are found in U.S. Pat. Nos. 2,747,334, 3,628,287, 3,846,937.

SUMMARY OF THE INVENTION

It is an object of the present invention to produce thebaine by the plant tissue culture of cells derived from Papaver bracteatum Lindl: population Arya II. This application of plant tissue culture technique can provide a method for the production of thebaine which is more economical than methods involving its ordinary extraction from grown plants. Moreover, the production of thebaine in virto, since it can be carried out under controlled conditions, may help to prevent the illicit use of thebaine in the preparation of narcotic medicaments.

According to the present invention there is provided a process for the production of thebaine which comprises the steps of:

(i) sterilising the surface of seed heads from Papaver bracteatum Lindl: population Arya II;

(ii) establishing aseptically callus tissue cultures of said seed heads in nutrient media;
(iii) growing said callus tissue cultures in said nutrient media;
(iv) subculturing said callus tissue cultures under aseptic conditions to form subcultures in fresh nutrient media;
(v) growing said subcultures;
(vi) subculturing said subcultures and growing further subcultures therefrom;
(vii) incubating and harvesting said further subcultures;
(viii) extracting the contents of cells grown in said further subcultures and media;
(ix) separating said contents from tissue and media;
(x) bringing said contents into contact with a non-aqueous solvent to form a solvent extract; and
(xi) isolating a thebaine-containing fraction of said solvent extract by chromatographic fractionation.

It is to be understood that the invention also extends to thebaine produced by the process of the invention and to codeine and morphine prepared therefrom.

There is also provided a process for the production of thebaine which comprises aseptically growing in a nutrient medium a plant tissue culture derived from Papaver bracteatum Lindl: population Arya II and isolating thebaine therefrom.

DESCRIPTION OF THE PREFERRED EMBODIMENTS

Tissue culture establishment

EXAMPLE 1

Surface sterilised seed heads from Papaver bracteatum Lindl: population Arya II were used to start a stationary (callus) tissue culture on solid revised tobacco medium supplemented with 0.5 to 5%, preferably about 1% agar and 0.1 to 2.0, suitably 1ppm, of 2,4-dichlorophenoxyacetic acid. The composition of revised tobacco medium is described in Staba, E. J. 1969, Plant tissue culture as a technique for the phyto-chemist, in Seikel, M. K. and V. C. Runeckles, Recent advances in phytochemistry Appleton-Century-Crofts, New York, 2:75. The medium used in the present method had a pH of 6 and the composition given in Table I.

Table I

| Constituents | |
|---|---|
| Inositol | 2.0g |
| Sucrose | 30.0g |
| Inorganic Stock Solution | 100.0ml |
| Complex Vitamin Concentrate | 10.0ml |
| Iron Stock Solution | 5.0ml |
| Double Distilled Water | to 1 litre | wherein:
Inorganic Stock Solution comprises:

| Stock Soln. A | | Medium mg/litre |
|---|---|---|
| MgSO$_4$.7H$_2$O | 7.4g | 370.0 |
| MnSO$_4$.H$_2$O | 0.338g | 23.3 |
| MnSO$_4$.7H$_2$O | 0.212g | 8.6 |
| Stock Soln. B | | |
| KNO$_3$ | 38.0g | 1900.0 |
| NH$_4$NO$_3$ | 33.0g | 1650.0 |
| Stock Soln. C | | |
| CaCl$_2$.2H$_2$O | 8.8g | 440.0 |
| KH$_2$PO$_4$ | 3.4g | 170.0 |
| H$_3$BO$_3$ | 0.124g | 6.2 |
| KI | 0.017g | 8.3 |
| Stock Soln. D | | |
| CuSO$_4$.5H$_2$O | 100ml<br>0.05g | 0.025 |
| Stock Soln. E | | |
| Na$_2$MoO$_4$.2H$_2$O | 100ml<br>0.50g | 0.25 |
| Stock Soln. F | | |
| CoCl$_2$.6H$_2$O | 100ml<br>0.05g | 0.025 |

Procedure:
Dissolve each ingredient of A, B and C in approximately 100ml H$_2$O. Mix A (sulfate) with B (nitrate) and add C (miscellaneous salts) separately. Add 1.0ml of each of D, E, and F. Dilute mixture with double distilled water in two liters.

Complex Vitamin Concentrate comprises:

| Vitamin | Stock mg/litre | Medium mg/litre |
|---|---|---|
| Cyanocobalamin | 0.15mg | 0.0015 |
| Folic Acid | 50.0mg | 0.5 |
| p-Amino Benzoic Acid | 50.0mg | 0.5 |
| Riboflavin | 50.0mg | 0.5 |
| Biotin | 100.0mg | 1.0 |
| Choline Chloride | 100.0mg | 1.0 |
| Ca Pantothenate | 100.0mg | 1.0 |
| Thiamin HCL | 100.0mg | 1.0 |
| Nicotinamide | 200.0mg | 2.0 |
| Pyridoxine HCL | 200.0mg | 2.0 |

Iron Stock Solution comprises:

| FeSO$_4$7H$_2$O | 5.57g |
|---|---|
| Na$_2$EDTA | 7.45g |

The cultures initially grew very slowly and after 2 to 3 weeks the tissues became dark brown in colour. Subculturing of the callus tissue was carried out and brought about the growth of new tissue which, although initially cream coloured, turned dark brown after 2 to 3 weeks. Addition of vitamin C to the medium at a concentration of 5 to 20ppm, more preferably about 10ppm, improved the appearance of the callus culture growth and lessened the browning of the tissue. After seven subcultures had been successively performed at 3 to 4 weekly intervals the seventh subculture was aseptically transferred to a 500ml Erlenmeyer flask containing 100ml liquid revised tobacco medium supplemented with 0.1ppm of 2,4-dichlorophenoxyacetic acid.

All callus cultures were incubated at 25° C. in the dark.

EXAMPLE 2

The same procedure was followed as in Example 1 except that the Erlenmeyer flask contained 100ml of Prairie Regional Laboratory B5 medium supplemented with 0.1ppm of 2,4-dichlorophenoxyacetic acid and adjusted to a pH of 5.5. As in Example 1, the callus culture was incubated in the dark at 25° C.

The make up of Prairie Regional Laboratory B5 medium is reported in Gamborg, O. L., R. Miller and K. Ojima; 1968, Nutrient requirements of suspension cultures of soybean root cells. Exp. Cell. Res. 50:151, and is given herein in Table II.

Table II

| Constituent | Quantity mg/litre |
|---|---|
| $NaH_2PO_4 \cdot H_2O$ | 150 |
| $KNO_3$ | 3000 |
| $(NH_4)_2SO_4$ | 134 |
| $MgSO_4 \cdot 7H_2O$ | 500 |
| $CaCl_2 \cdot 2H_2O$ | 150 |
| Iron | 28 |
| Nicotinic Acid | 1 |
| Thiamine . HCl | 10 |
| Pyrodoxine . HCl | 1 |
| m-Inositol | 100 |
| $MnSO_4 \cdot H_2O$ | 10 |
| $H_3BO_3$ | 3 |
| $ZnSO_4 \cdot 7H_2O$ | 2 |
| $Na_2MoO_4 \cdot 2H_2O$ | 0.250 |
| $CuSO_4$ | 0.025 |
| $CoCl_2 \cdot 6H_2O$ | 0.025 |
| KI | 0.750 |
| Sucrose | 20,000 |
| 2,4-D | 2 |

EXAMPLE 3

The same procedure was followed as in Example 1 except that after transference to the Erlenmeyer flask the culture was incubated at 25° C. on a gyratory shaker at 80 rpm with continuous 24 hour ordinary room lighting. A suspension culture was successfully established which was transferred every two weeks to a fresh sample of revised tobacco medium. The fifth generation of suspension culture was harvested for chemical analysis.

EXAMPLE 4

The same procedure was followed as in Example 1 except that the Erlenmeyer flask contained 100ml of Prairie Regional Laboratory B5 medium supplemented with 0.1ppm of 2,4-dichlorophenoxyacetic acid and that the culture was incubated at 25° C. on a gyratory shaker at 80 rpm with continuous 24 hour ordinary room lighting. As in Example 3, a suspension culture was successfully established by this method.

Extraction

A sufficient number of fifth generation cultures of Example 3 were grown and collected to provide a suitable sample for chemical analysis. The contents of the grown cells were extracted by adjusting the pH of the harvested cultures (tissue and medium) to 2.0 by the addition of 1% HCl and stirring overnight on a magnetic stirrer. The tissues were then removed by filtration. The pH of the filtrate was adjusted to 9.0 by the addition of concentrated ammonium hydroxide. Chloroform was added to the filtrate and the resulting chloroform extract was concentrated under reduced pressure.

Isolation and identification of thebaine

Preparative thin-layer chromatography was used to isolate the thebaine. The chloroform extract was applied on silica gel (GF-254 obtained from E. Merck, A. G., Darmstadt, Germany) and developed with chloroform-methanol (9:1). Plates were observed under ultraviolet light to detect fluoroescent spots at 254nm followed by spraying with Dragendorff's (potassium-iodobismuthate), or iodoplatinic acid spray reagents. A fraction having an $R_f$ value identical to that of an authentic thebaine sample was obtained which was eluted with chloroform and used for further analysis.

Thin layer chromatography of the eluted fraction was carried out in three different solvent systems: acetone-methanol-triethylamine (98:1:1); acetone-ammonia (9:1); and ethyacetate-methanol-ammonia (85:10:5). Examination of the chromatograms under ultraviolet light at 254nm revealed a fluorescent spot with an $R_f$ value identical to that of an authentic thebaine sample. When the plates were sprayed with Dragendorff's or iodoplatinic acid spray reagents one single spot similar in colour and $R_f$ value to that of authentic thebaine appeared.

The ultraviolet spectrum (run on a Beckman model DB-GT spectrophotometer) of the eluted fraction in 0.1 N HCl had an adsorption maximum at 285nm which is the same as for the authentic thebaine. A comparison of the extinction co-efficient of the thebaine obtained by the present method with that of a standard solution of authentic thebaine indicated a yield of 0.1% thebaine based on the dry weight of the seed head tissue.

The eluted fraction was also qualitatively analysed by gas liquid chromatography using a Beckman model GC-65 gas chromatograph with flame ionisation detector on 0.5% OV-1 column (1.3m × 2mm) packed with Gas Chrom-Q (80–100 mesh) with the column at 220°, detector 230°, injector 240°, and $N_2$ at 20ml/min). Retention time of the isolated alkaloid corresponded to that of the authentic thebaine sample and when the two were co-chromatographed a single peak appeared with a retention time similar to that of authentic thebaine.

Recently, it was reported (Maghssoudi, R. H. and A. B. Fawzi. 1976, Direct spectrophotometric determination of thebaine in the Arya II population capsules of Papaver bracteatum Lindl. J. Pharm. Sci. (in press)), that thebaine forms a complex with bromocresol green which, in chloroform has an adsorption maximum at 415nm. This was confirmed with the isolated fraction. In addition, the thebaine content of the isolated fraction from tissue culture was confirmed with concentrated sulphuric acid which produced a red colour (Reffer, I. and K. Toczko. 1956, A micromethod for the colorimetric determination of the five major alkaloids in opium, Acta Biochem. Polon. 3:381).

Control extraction and isolation procedures were carried out on fresh un-inoculated medium to ensure that there was no artifact due to the constituents of the medium.

Attempts to start stationary (callus) tissue cultures from surface sterilised stems and leaves of Papaver bracteatum Lindl:population Arya II on revised tobacco medium and on Prairie Regional Laboratory B5 medium containing various concentrations of 2,4-dichlorophenoxyacetic acid proved unsuccessful.

A herbarium sample of the plant material has been deposited in the Missouri Botanical Garden. For the tissue culture, the 1974 collection was used.

We claim:
1. A process for the production of thebaine which comprises the steps of:
  (i) sterilising the surface of seed heads from Papaver bracteatum Lindl:population Arya II;
  (ii) establishing aseptically callus tissue cultures of said seed heads in nutrient media;
  (iii) growing said callus tissue cultures in said nutrient media;
  (iv) subculturing said callus tissue cultures under aseptic conditions to form subcultures in fresh nutrient media;
  (v) growing said subcultures;
  (vi) subculturing said subcultures and growing further subcultures therefrom;

(vii) incubating and harvesting said further subcultures;
(viii) extracting the contents of cells grown in said further subcultures and media;
(ix) separating said contents from tissues and media;
(x) bringing said contents into contact with a non-aqueous solvent to form a solvent extract; and
(xi) isolating a thebaine-containing fraction of said solvent extract by chromatographic fractionation.

2. A process as claimed in claim 1 wherein the culture is a callus tissue culture and the nutrient medium comprises revised tobacco medium and at least one growth regulating agent.

3. A process as claimed in claim 2 wherein the callus tissue culture is grown in a first revised tobacco medium containing agar and 2,4-dichlorophenoxyacetic acid in growth regulating amounts and a subculture of said callus tissue culture is grown in a second revised tobacco medium.

4. A process as claimed in claim 1 wherein the culture is a callus tissue culture which is grown in a first nutrient medium comprising revised tobacco medium and at least one growth regulating agent and a subculture of the said callus tissue culture is grown in a second medium comprising Prairie Regional Laboratory B5 medium and at least one growth regulating agent.

5. A process as claimed in claim 1 wherein the culture is firstly a callus tissue culture grown in a first nutrient medium comprising revised tobacco medium and at least one growth regulating agent and is secondly a subculture of said callus tissue culture grown as a suspension tissue culture in a liquid medium comprising revised tobacco medium and at least one growth regulating agent.

6. A process as claimed in claim 1 wherein the culture is firstly a callus tissue culture grown in a first nutrient medium comprising revised tobacco medium and at least one growth regulating agent and is secondly a subculture of said callus tissue culture grown as a suspension culture in a liquid medium comprising Prairie Regional Laboratory B5 medium and at least one grown regulating agent.

7. A process as claimed in claim 1 wherein thebaine is isolated from the culture by solvent extraction and chromatorgraphic fractionation.

* * * * *